United States Patent [19]

Montada

[11] Patent Number: 4,489,766
[45] Date of Patent: Dec. 25, 1984

[54] SYRINGE FILLING DEVICE

[76] Inventor: Benjamin V. Montada, 309 Louis Dr., Mississauga, Ontario, Canada, L5B 1Z2

[21] Appl. No.: 426,760

[22] Filed: Sep. 29, 1982

[30] Foreign Application Priority Data

Sep. 13, 1982 [CA] Canada .................................. 411299

[51] Int. Cl.³ .............................................. B65B 3/04
[52] U.S. Cl. ..................................... 141/27; 604/407; 222/309; 141/375; 141/95
[58] Field of Search ............. 141/27, 18, 21, 231–233, 141/311, 318, 319, 328, 329, 330, 367–369, 375.2, 94–96; 604/407, 414; 222/309; 73/864.16, 864.18

[56] References Cited

U.S. PATENT DOCUMENTS

| | | | |
|---|---|---|---|
| 2,861,570 | 11/1958 | Beecher | 604/407 |
| 3,578,037 | 5/1971 | Flynn | 141/27 |
| 3,833,030 | 9/1974 | Waldbauer, Jr. et al. | 141/26 |
| 3,875,979 | 4/1975 | Holts | 141/27 |
| 3,907,009 | 9/1975 | Dobbins | 141/27 |
| 4,077,750 | 3/1978 | Hake | 222/309 X |
| 4,252,159 | 2/1981 | Maki | 141/27 |

FOREIGN PATENT DOCUMENTS 2939110 4/1981 Fed. Rep. of Germany ...... 604/414

OTHER PUBLICATIONS

Morris Watts Insulin Gauge–Canadian National Inst. for Blind–Instruction Sheet Vancouver B.C.
Insulin Gauge–Andros, Inc. Berkeley, Ca.

Primary Examiner—Stephen Marcus
Assistant Examiner—Ernest G. Cusick
Attorney, Agent, or Firm—Moss, Hammond

[57] ABSTRACT

A device is shown for filling a syringe with a desired quantity of medicine, such as insulin, and is particularly useful for blind people or people with impaired vision who cannot read or see the volume markings on a syringe. The device has an elongate body with a syringe recess for retaining a syringe in position. A bottle recess is provided in the elongate body for sliding a medicine bottle onto the needle of the syringe. The elongate body has a gauge recess adjacent to the position where the syringe plunger would be located allowing the syringe plunger to be fully extracted. A plurality of retractable spacers of different thicknesses are located in the gauge recess to limit the extraction of the syringe plunger and thus gauge or control the quantity of medicine drawn into the syringe. The spacers are rearrangeable and removable to preselect the medicine dosage filling the syringe.

4 Claims, 5 Drawing Figures

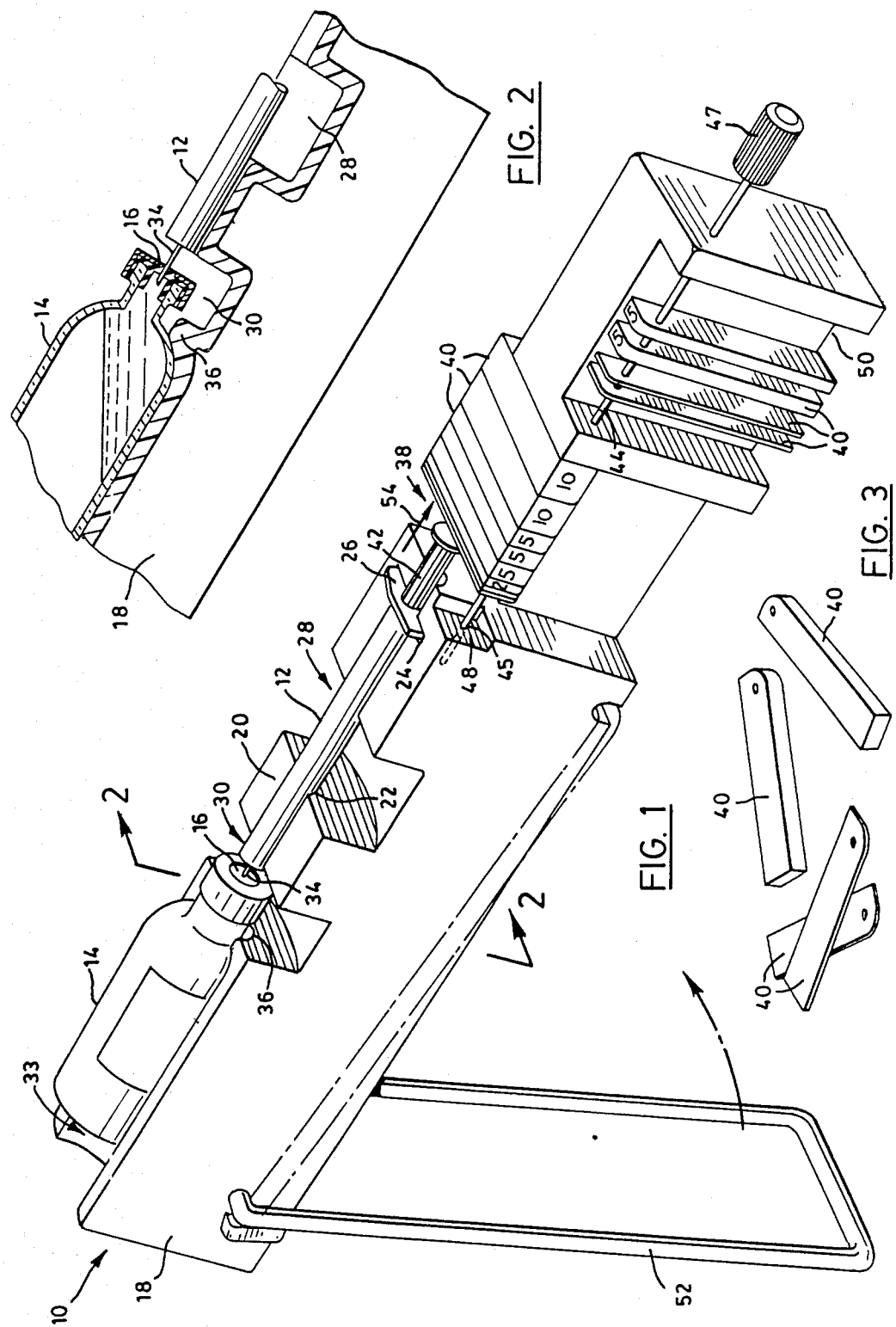

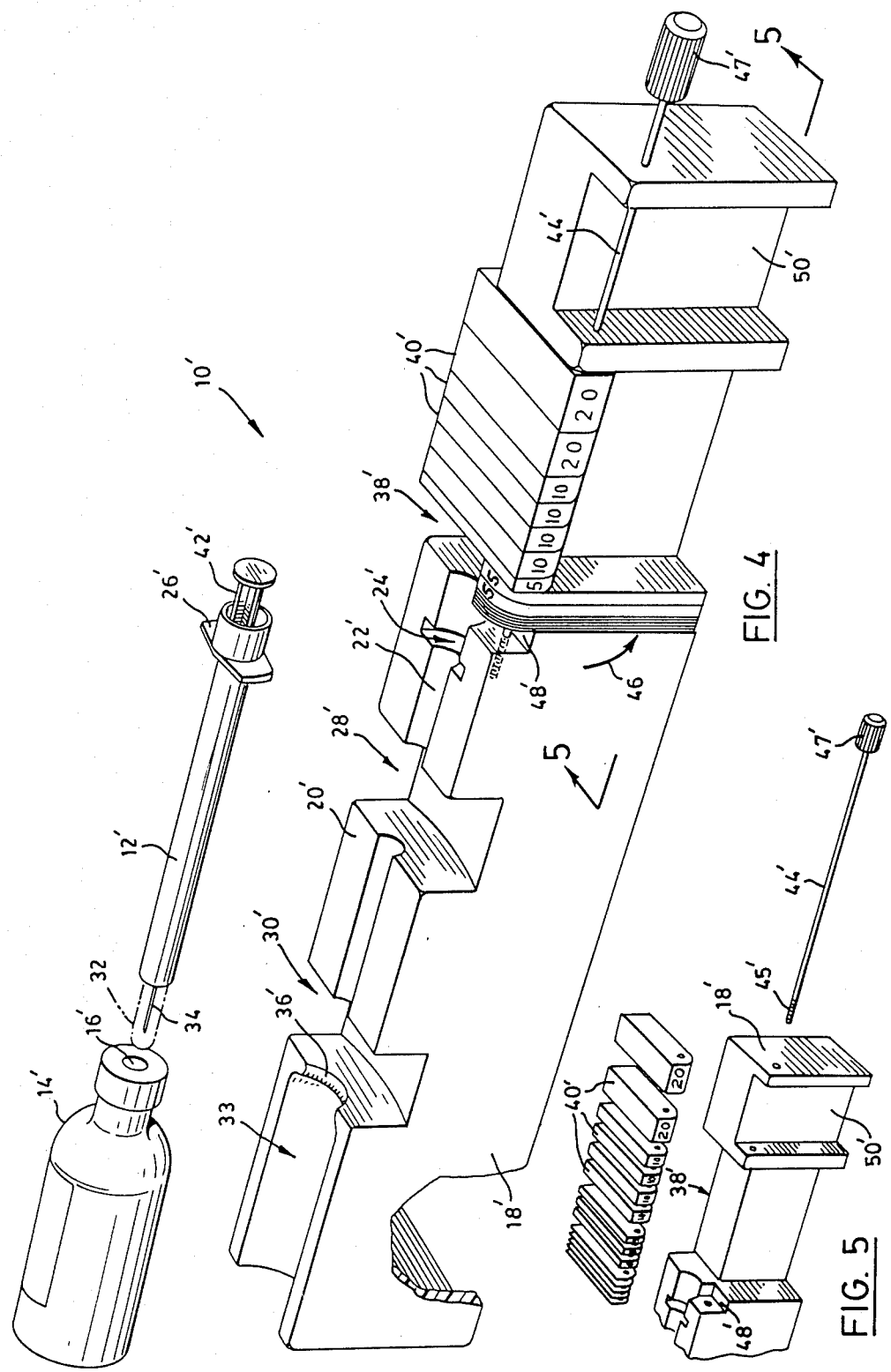

SYRINGE FILLING DEVICE

BACKGROUND OF THE INVENTION

This invention relates to gages or measuring devices for filling syringes with medicine, such as insulin.

Many people are required to self-administer doses of medicine using syringes. For a normal person, this is usually not a problem, because the syringes are clearly marked as to fill quantity and are fairly easy to manipulate. However, for people who are blind or have impaired eyesight or similar disabilities, filling a syringe accurately and conveniently is difficult, if not impossible. This is particularly common in the case of diabetics who frequently suffer from impaired vision or blindness. Not only is there a problem of not being able to see the quantity markings on the syringe, but frequently there is inability or difficulty involved in putting the syringe needle into the medicine bottle. The needle may be guided or touched with the fingers rendering the needle unsterile, and sometimes the needle is bent or broken in the process.

In the past, diabetics as home who are unable to see to prepare their own insulin dosages had to rely on another person to fill the syringes for them. Obviously, if another person was not available, a daily insulin injection could be missed or at least delayed endangering the person's health.

As a partial solution to this problem, insulin gages have been produced in the past in the form of a plastic strip having an opening for locating a syringe barrel flange therein. The plastic strip can then be cut to length corresponding to the distance the syringe plunger should be withdrawn to fill the syringe with the desired dosage. A difficulty with this plastic strip type gage, however, is that the gage must first be cut to the desired length by a person with normal eyesight. Also, once the gage has been cut, it cannot be used again for larger doses if it is necessary to increase the level of medication for the patient.

As an improvement on the plastic strip type insulin gage, another type of gage has been produced wherein adjustable stops are provided on the body of the gage rather than cutting the gage to length for a particular dosage. While this type of gage can be adjusted for larger or smaller doses, it is still necessary to have a person with normal eyesight make the adjustments. Also, in the prior art adjustable stop type gages there is usually nothing to guide the syringe needle into the medicine bottle, so it is still likely that the needle will be touched making it unsterile.

SUMMARY OF THE INVENTION

In the present invention, an elongate body is provided to hold a syringe and the plunger of the syringe is engaged by a preselected number of individually retractable spacers to measure the dosage, the spacers being simply and easily manipulated even by a blind person making the filling of the syringe convenient and accurate.

According to the invention, there is provided a syringe filling device comprising an elongate body having an upper face defining a central axis syringe recess for removably positioning a syringe and preventing the syringe from moving axially. The body has means for exposing the needle of a syringe for insertion thereof into a medicine bottle. The upper face also has a gage recess located adjacent to the syringe recess where the plunger of a syringe would be located, the gage recess permitting a syringe plunger to be fully extracted. Also, a plurality of spacers retractably fill the gas recess, the spacers being individually retractable to limit selectively the extraction of a syringe plunger.

BRIEF DESCRIPTION OF THE DRAWINGS

A preferred embodiment of the invention will now be described, by way of example, with reference to the accompanying drawings, in which:

FIG. 1 is a perspective view of a preferred embodiment of a syringe filling device according to the invention showing the device used in association with a syringe and medicine bottle;

FIG. 2 is a partial sectional view taken along lines 2—2 of FIG. 1;

FIG. 3 is a perspective view of some spacers as used in the embodiment shown in FIG. 1;

FIG. 3 is a perspective view of another embodiment of a syringe filling device according to the present invention showing a syringe and medicine bottle removed from the device; and FIG. 5 is an exploded perspective view of a portion of the embodiment shown in FIG. 4 taken along lines 5—5 of FIG. 4.

DETAILED DESCRIPTION OF THE PREFERRED EMBODIMENT

Referring to the drawings, a preferred embodiment of a syringe filling device is generally indicated by reference numeral 10. Like reference numerals are used throughout the drawings to indicate similar parts, primed reference numerals being used for the embodiment shown in FIGS. 4 and 5. Device 10 is used in association with a syringe 12, which is typically of the plastic disposable type. Device 10 is also used with a medicine bottle 14, which typically is a glass bottle having a top with a rubber seal 16. Syringe 12 and medicine bottle 14 are conventional and are not part of the present invention, so they will not be described in further detail herein. However, as mentioned below, syringe filling device 10 must be dimensioned or calibrated to suit a particular brand of syringe 12 or medicine bottle 14, to the extent that the dimensions of these items vary in the marketplace. It should be noted, however, that most medicine bottles 14 are standard in size, and that there are only a few manufacturers of plastic disposable syringes 12, so there are not many dimensional variations in practice. This is particularly the case in connection with insulin and insulin syringes.

Syringe filling device 10 has an elongate body 18, which is typically made of plastic and is either hollow or U-shaped in transverse cross-section as seen best in FIGS. 2 and 4. Elongate body 18 has an upper face 20 which has a central axial syringe recess 22 (see FIG. 4). Syringe recess 22 is dimensioned to accommodate a plastic disposable syringe 12, and for this purpose has a transverse syringe flange recess portion 24 into which a syringe flange 26 is located to prevent the syringe barrel from moving axially. Syringe recess 22 also includes a transverse barrel access recess portion 28 for gripping the barrel of syringe 12 with the fingers to remove the syringe from device 10 after the syringe is filled. Syringe recess 22 also includes a transverse cover access recess portion 30 for gripping and removing a syringe needle cover 32 (shown in chain dotted lines in FIG. 4)

after the syringe is positioned in syringe filling device 10.

The body upper face 20 also includes a bottle recess 33 located adjacent to syringe recess 22, and in particular, adjacent to cover access recess 30. The bottle recess 33 is in the form of an elongate channel for sliding medicine bottle 14 axially onto a needle 34 of syringe 12. The bottle recess 33 includes a neck portion 36 adjacent to syringe recess 22. The neck portion 36 longitudinally limits the sliding travel of medicine bottle 14 into syringe needle 34, so that needle 34 penetrates the top of medicine bottle 14 far enough to communicate with the fluid inside bottle 14 but not too far. If needle 34 projects too far into bottle 14, there is some risk that air will be drawn into syringe 12 during filling as the content of medicine bottle 14 is depleted.

The body upper face 20 also includes a gage recess 38 located adjacent to the syringe recess 22. Gage recess 38 is filled with a plurality of spacers 40 which limit the movement of a syringe plunger 42 as seen best in FIG. 1. If spacers 40 were removed, plunger 42 would be permitted to be fully extracted into gage recess 38. However, spacers 40 limit the extraction of plunger 42 and thus gage and control the amount of fluid or dosage drawn into syringe 12, as seen best in FIG. 1.

Spacers 40 are pivotally or retractably mounted in gage recess 38 by a pivot pin 44 having a threaded end portion 45 which is screwed into body 18. Spacers 40 thus being pivotally mounted on pivot pin 44 retractably fill gage recess 38 and are individually retractable to limit selectively the extraction of syringe plunger 42. As seen best in FIG. 4, spacers 40, 40' may be pivoted up and around out of the way in the direction of arrow 46 to rest in a side inactive portion of gate recess 38.

Spacers 40 are of different thicknesses corresponding to preselected volumes of syringe capacity. For example, if a spacer 40 was marked with the reference numeral 10, it would be of a thickness such that longitudinal movement of plunger 42 equal to the thickness of such spacer would cause syringe 12 to draw in or expel ten units (0.1 cubic centimeters) of medicine. Similarly, other spacers are of such thicknesses that longitudinal movement of syringe plunger 42 causes the syringe 12 to draw in or expel one unit, two units, five units, or any other desired denomination. In the embodiment shown in FIG. 1, the total thickness of all of the spacers 40 that will fit into gage recess 38 is equivalent to fifty units of travel of syringe plunger 42, so a fifity unit or 0.5 cc syringe could be used with syringe filling device 10. Similarly, in the embodiment shown in FIG. 4, the total thickness of all of the spacers 40' that can fit into gage recess 38' is equivalent to one hundred units of travel of syringe plunger 42', so syringe 12' would be a one hundred unit or 1.0 cc syringe.

As seen best in FIGS. 1 and 5, pivot pins 44, 44' have knobs 47, 47', so that the pivot pins may be unscrewed and removed longitudinally thus making spacers 40, 40' removable and interchangeable in longitudinal position in the gage recess 38. Gage recess 38 includes a pivot pin seat recess portion 48 to facilitate the reinsertion of pivot pin 44 by ensuring that the threaded hole into which threaded end portion 45 is screwed is always visible even if spacers 40 are at the extreme forward end of gage recess 38.

Spacers 40 are normally arranged in the gage recess 38 in order to thickness, the thinner spacers being located adjacent to syringe recess 22. However, it will be appreciated that the spacers can be rearranged in any desired order, and this may be necessary if the dosage to which syringe 11 must be filled is an odd number of units. Elongate body 18 is provided with a spacer storage recess 50 for storing extra spacers 40, or the spacers 40 that have been removed from gage recess 38. It will be appreciated that pivot pin 44 removably retains the spare spacers 40 in the spacer storage recess 50 in much the same manner as the spacers 40 are retained in gage recess 38.

Syringe filling device 10 also includes a support stand 52 hingeably attached to an end portion of elongate body 18 adjacent to bottle recess 33. The support stand 52 is dimensioned to retain elongate body 18 in an upright position as shown in FIG. 1 with the bottle recess and thus bottle 14 elevated.

In the embodiment shown in FIG. 4, it will be noted that the support stand 52 has been eliminated. In use, syringe filling device 10' is simply held in an upright or vertical position while filling syringe 12'. As mentioned above, syringe filling device 10' is a one hundred unit device for one hundred unit syringes, so appropriate modifications have been made to accommodate a larger syringe and a larger number of spacers 40'.

In use, a syringe 12 is placed on syringe filling device 10 in syringe recess 22 and held in position by a person's thumb or fingers pressing on the syringe barrel. The appropriate number of spacers 40 according to the dosage required are pivoted out of the path of syringe plunger 42. Alternatively, the appropriate number of spacers 40 for the dosage required may have been previously removed. This would be preferable if the same dosage is given repeatedly, as then it would not be necessary to adjust or check the number of spacers remaining in the gage recess for each filling of the syringe 12.

Once the spacers 40 have been arranged as desired, the syringe needle cover 32 is removed using a thumb and forefinger in cover access recess 30 to wiggle the needle cover loose. Syringe plunger 42 is then pulled down in the direction of arrow 54 to engage the spacers 40 remaining in gage recess 38. The syringe is now filled with air equivalent to the number of units of the medicine dosage required (it will be noted that this is the same number of units for which spacers 40 have been moved out of the path of plunger 42). Medicine bottle 14 is then placed in bottle recess 33 (after having had the seal 15 swabbed with alcohol), and the medicine bottle is slid down onto needle 34 causing the needle to penetrate the bottle.

Plunger 42 is then pushed up into the syringe barrel injecting air into the medicine bottle 14. Syringe filling device 10 is then held upright or vertical and plunger 42 is extracted to contact again spacers 40 and thus fill the syringe with the desired dose of medicine. Medicine bottle 14 is then slid off the syringe and the syringe removed from syringe filling device 10 for use.

In some situations, it is desirable to fill a syringe with two types of medicine. In this case, spacers 40 are first adjusted to measure the quantity of medicine which is the largest of the two types to be used. The syringe is placed in device 10 as mentioned above, the plunger 42 withdrawn to contact spacers 40, and the appropriate medicine bottle is slid onto the syringe needle as described above. The syringe plunger 42 is then pushed all the way up to inject air into the medicine bottle equivalent to the dosage of that particular medicine required. The bottle 14 is then removed and the spacers 40 are readjusted to measure the dosage of the medicine of which a smaller quantity is required. Plunger 42 is extracted to contact the readjusted spacers and the second medicine bottle is then slid down onto needle 34 in a manner similar to that described above. Plunger 42 is then pushed all of the way up to inject air into the second medicine bottle. Device 10 is held upright and the plunger extracted to fill the syringe with the desired quantity of the second medicine (the medicine of which a smaller quantity is required). The second medicine bottle is removed and the first bottle is again slid down onto syringe needle 34. The spacers 40 are again readjusted to the larger quantity dosage (i.e., spacers equivalent to the larger dosage are removed from the path of plunger 42) and the syringe plunger 42 is extracted further to contact the readjusted spacers, thus filling the syringe from the first medicine bottle with the larger quantity medicine. The syringe is thus filled as desired with both types of medicine.

Having described preferred embodiments of the invention, it will be appreciated that various modifications may be made to the structures described. For example, spacers 40 could be retractably held in position in a different manner, such as by arranging them to slide into or out of the path of a syringe plunger 42. For the purposes of the present specification, the term "retractable" is intended to include all methods of making spacers 40 move into or out of the path of a syringe plunger 42, including making the spacers removable. The elongage body 18 could be made without a bottle recess 33, since a person could hold the medicine bottle by hand when using the syringe filling device 10. However, as mentioned above, there is some risk in this case that a blind person may need to touch the syringe needle making it unsterile. Obviously, syringe filling device 10 can be made other sizes and shapes as desired.

From the above, it will be appreciated that the present invention provides a very simple, efficient and accurate device for filling a syringe, which is particularly useful for blind people or others having disabilities making it difficult to fill syringes in the normal manner.

What I claim as my invention is:

1. A device for filling a syringe having a needle and an axially movable plunger, the device comprising: an elongate body having a body upper face defining a central axial syringe recess for removably positioning a syringe therein and preventing said syringe from moving axially, the body having means for exposing the needle of a syringe for insertion thereof into a medicine bottle; the upper face also having a longitudinal gage recess located adjacent to the syringe recess where the plunger of a syringe would be located, the gage recess being of a longitudinal length equal to a fully extracted syringe plunger; a plurality of spacers retractably filling said gage recess, the spacers being individually retractable to. limit selectively the extraction of a syringe plunger, the spacers being of different thicknesses corresponding to preselected volumes of syringe capacity, the total thickness of said spacers being equal to the longitudinal travel of a fully extracted syringe plunger; the elongate body further including a spacer storage recess; and means for removably retaining the spacers in said spacer storage recess.

2. A device for filling a syringe having a needle and an axially movable plunger, the device comprising: an elongate body having a body upper face defining a central axial syringe recess for removably positioning a syringe therein and preventing said syringe from moving axially; the body having means for exposing the needle of a syringe for insertion thereof into a medicine bottle; the upper face also having a longitudinal gage recess located adjacent to the syringe recess where the plunger of a syringe would be located, the gage recess being of a longitudinal length equal to a fully extracted syringe plunger; a plurality of spacers retractably filling said gage recess, the spacers being individually retractable to limit selectively the extraction of syringe plunger, the spacers being of different thicknesses corresponding to preselected volumes of syringe capacity, the total thickness of said spacers being equal to the longitudinal travel of a fully extracted syringe plunger; and a support stand hingeably attached to an end portion of the elongate body adjacent to the bottle recess, the support stand being dimensioned to retain the elongate body in an upright position with the bottle recess elevated.

3. A device for filling a syringe having a needle and an axially movable plunger, the device comprising: an elongate body having a body upper face defining a central axial syringe recess for removably positioning a syringe therein and preventing said syringe from moving axially; the body having means for exposing the needle of a syringe for insertion thereof into a medicine bottle; the upper face also having a longitudinal gage recess located adjacent to the syringe recess where the plunger of a syringe could be located, the gage recess being of a longitudinal length equal to a fully extracted syringe plunger; a plurality of removable and interchangeable spacers retractably filling said gage recess, the spacers being individually retractable to limit selectively the extraction of syringe plunger, the spacers being of different thicknesses corresponding to preselected volumes of syringe capacity, the total thickness of said spacers being equal to the longitudinal travel of a fully extracted syringe plunger, a longitudinally movable pivot pin located adjacent to one side of said gage recess, the spacers being pivotally mounted on the pivot pin to pivot into and out of the path of a syringe plunger; the gage recess including a pivot pin seat recess portion; the elongate body further including a spacer storage recess; and further comprising means for removably retaining spacers in said spacer storage recess.

4. A device for filling a syringe having a needle and an axially movable plunger, the device comprising: an elongate body having a body upper face defining a cental axis syringe recess for removably positioning a syringe therein and preventing said syringe from moving axially; the body having means for exposing the needle of a syringe for insertion thereof into a medicine bottle; the upper face also having a longitudinal gage recess located adjacent to the syringe recess where the plunger of a syringe would be located, the gage recess being of a longitudinal length equal to a fully extracted syringe plunger; a plurality of spacers retractably filling said gage recess, the spacers being individually retractable to limit selectively the extraction of a syringe plunger, the spacers being of different thicknesses corresponding to preselected volumes of syringe capacity, the total thickness of said spacers being equal to the longitudinal travel of a fully extracted syringe plunger; and a support stand hingeably attached to an end portion of the elongate body adjacent to the bottle recess, the support stand being dimensioned to retain the elongate body in an upright position with the bottle recess elevated.

* * * * *